(12) United States Patent
Franconi et al.

(10) Patent No.: US 8,380,282 B2
(45) Date of Patent: Feb. 19, 2013

(54) METHOD FOR ACQUIRING ELECTROMAGNETIC SIGNALS AND CONTRAST PRODUCT THEREFOR

(75) Inventors: Jean-Michel Franconi, Merignac (FR); Sylvain Miraux, Merignac (FR); Eric Thiaudiere, Bordeaux (FR); Paul Canioni, Pessac (FR)

(73) Assignees: Centre National de la Recherche and Scientifique—CNRS, Paris (FR); Universite Victor Segalen Bordeaux 2, Bordeaux (FR)

( * ) Notice: Subject to any disclaimer, the term of this patent is extended or adjusted under 35 U.S.C. 154(b) by 0 days.

(21) Appl. No.: 12/831,194

(22) Filed: Jul. 6, 2010

(65) Prior Publication Data
US 2011/0144477 A1    Jun. 16, 2011

Related U.S. Application Data

(63) Continuation of application No. 10/583,826, filed as application No. PCT/FR03/03628 on Dec. 8, 2003, now abandoned.

(30) Foreign Application Priority Data

Dec. 13, 2002 (FR) ..................... 02 15826

(51) Int. Cl.
*A61B 5/05* (2006.01)
(52) U.S. Cl. ........ 600/410; 600/407; 600/421; 600/420; 600/424; 424/9.34; 424/1.11; 424/1.65

(58) Field of Classification Search ............... 600/407, 600/410, 421, 420, 424; 424/9.34, 1.11, 424/1.65
See application file for complete search history.

(56) References Cited

U.S. PATENT DOCUMENTS

| | | | |
|---|---|---|---|
| 6,770,261 B2 * | 8/2004 | Meade et al. | 424/9.34 |
| 2003/0064023 A1 * | 4/2003 | Driehuys et al. | 424/9.3 |

* cited by examiner

*Primary Examiner* — Brian Casler
*Assistant Examiner* — Joel Lamprecht
(74) *Attorney, Agent, or Firm* — Blakely, Sokoloff, Taylor & Zafman

(57) ABSTRACT

The invention concerns a system capable of generating a magnetic indication $B_0$ comprising gradients ($G_x$, $G_y$, $G_z$) in certain directions, transmitting ratio frequency wave pulse sequences (RF) perpendicular to $B_0$ in a range of adjustable frequencies, and detecting electromagnetic signals received from a body part (4). The method includes injecting a contrast product in said body part, capable of being temporarily fixed in an observed zone (1), and comprising an element capable of causing chemical displacement of a resonance frequency of water hydrogen protons; exciting said body part, using a radio wave pulse sequence; in a range of frequencies adjusted on the basis of the magnetic induction $B_0$ and the chemical displacement for some of said waves; detecting the electromagnetic signals received in said body part, substantially corresponding to the magnetic resonance signals of the protons of the observed zone having undergone the chemical displacement.

15 Claims, 1 Drawing Sheet

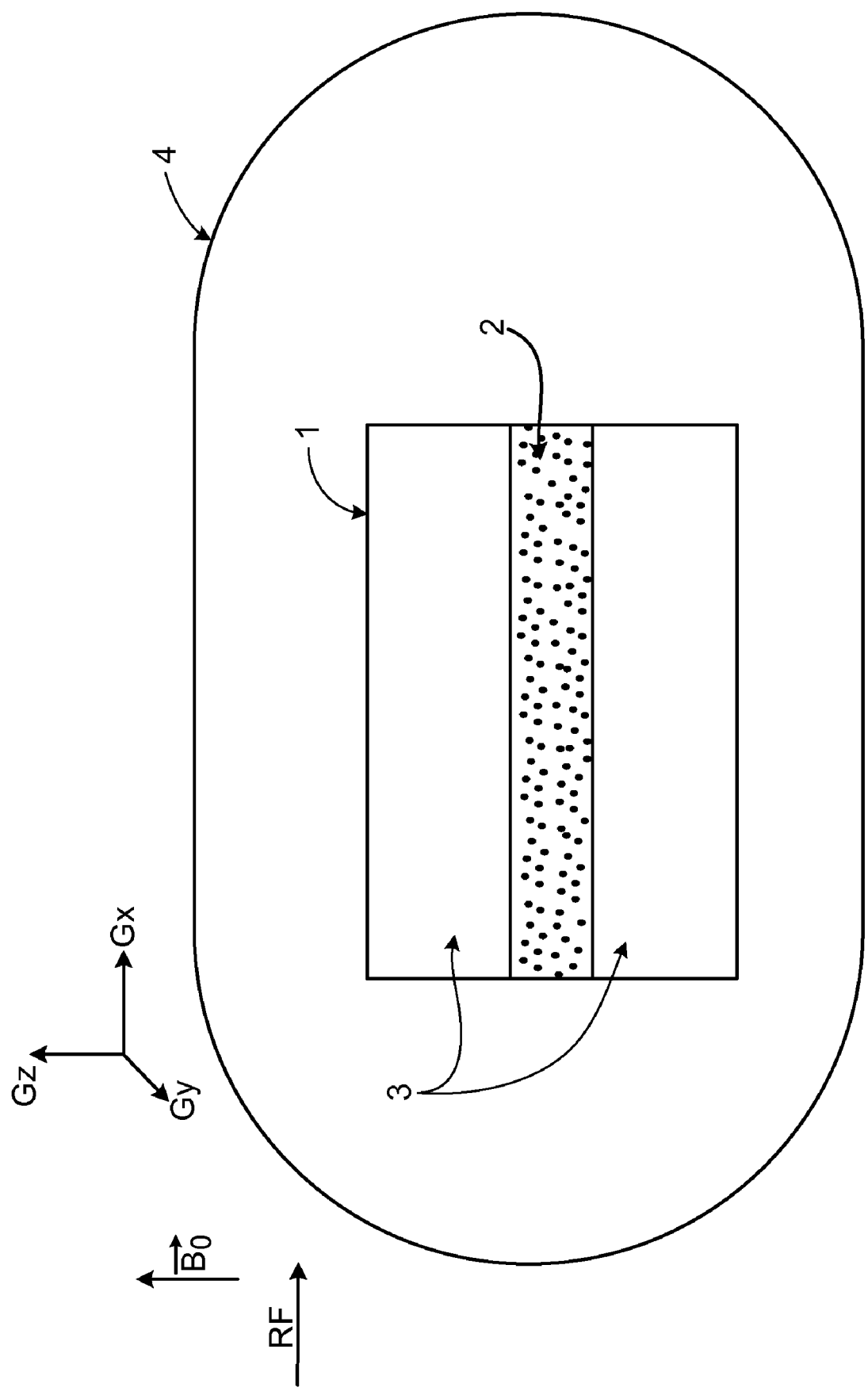

METHOD FOR ACQUIRING ELECTROMAGNETIC SIGNALS AND CONTRAST PRODUCT THEREFOR

CROSS-REFERENCE TO RELATED APPLICATIONS

This application is continuation of U.S. application Ser. No. 10/538,826 filed Jun. 13, 2005 now abandoned, which claims the benefit of the National Stage of International Application No. PCT/FR2003/003628, filed Dec. 8, 2003, which claims the benefit of French Patent Application Serial No. 02/15,826, filed on Dec. 13, 2002. The contents of these applications are hereby incorporated by reference in their entireties.

BACKGROUND OF THE INVENTION

The present invention relates to the acquisition of electromagnetic signals. It relates more particularly to the acquisition of such signals received from a body part, in particular a human or animal body part, in response to an external electromagnetic solicitation.

Various methods for acquiring signals are known, in particular in the magnetic resonance imaging (MRI) field. These methods have common characteristics.

They generally consist in subjecting the body in question to a high-intensity magnetic induction $B_0$, typically between 0.1 and 3 Tesla. The effect of this induction is to orient the magnetic moments of the protons of the hydrogen contained in the water molecules of the body in a direction close to the main direction of the magnetic induction $B_0$.

The body part imaged is then subjected to a radiofrequency wave applied perpendicular to the magnetic induction $B_0$ and the frequency of which is typically adjusted to the Larmor precession frequency of the hydrogen nucleus in the magnetic induction $B_0$ in question. This frequency is proportional to the intensity of the magnetic induction $B_0$ and has the specificity of bringing into resonance the protons of the hydrogen contained in the water molecules of the body. By way of example, for an induction $B_0$ of 1 Tesla, the corresponding Larmor frequency is in the region of 42 MHz.

Immediately after the transmission of this radio frequency wave, the magnetic moments that have been subjected to the wave begin to oscillate around their equilibrium position and again take up a position along their original direction, close to that of the magnetic induction $B_0$. This phenomenon is known as proton relaxation.

During the relaxation, each water proton that has come into resonance creates, as a result, a relatively weak electromagnetic signal, called a magnetic resonance signal. This signal can then be detected by means of an appropriate detection module.

Gradients of the magnetic induction $B_0$ can be used in various spatial directions, so as to have different induction values between two points in space, each corresponding to an elementary volume of the body in question.

The use of magnetic induction $B_0$ gradients therefore allows spatial localization of the signal. The step of coding the space by means of the gradients is carried out between the proton excitation and the magnetic resonance signal reception. These basic principles give rise to different methods of exploitation so as to allow the production of a selective image for a chosen element of the body observed, for example a blood vessel.

In a first method, referred to as "time of flight" method, the radio frequency waves are transmitted repeatedly and regularly, in a train of pulses. The repetition of these waves is adjusted so as to be sufficiently frequent for the proton relaxation not to have time to be entirely complete before transmission of the next wave. This saturation phenomenon means that the magnetic resonance signal is greatly reduced. It virtually makes it possible to eliminate the signals transmitted by the immobile protons, i.e. typically the protons that are part of tissues of the body in question.

On the other hand, mobile protons that penetrate the zone in question without having been subjected beforehand to a train of pulses come into resonance and create a magnetic resonance hypersignal that can be detected. The mobile protons are typically the protons contained in the water of the circulating blood.

This time of flight method therefore makes it possible to distinguish between the relaxed mobile protons and the saturated immobile protons and thus makes it possible to isolate a selective signal corresponding, for example, to a blood activity. This method can in particular be applied in the field of angiography, since it makes it possible to detect a signal originating from a blood vessel in particular.

It is, however, limited to the analysis of blood vessels that are short and have a high flow rate, since, if the opposite is true, the protons contained in the blood circulating in these vessels rapidly undergoes saturation, like the protons of the surrounding tissues.

A second method, referred to as "phase contrast" method, takes advantage of the relationship that exists between the phase of the detected magnetic resonance signal and the rate of proton displacement in the body in question, to allow detection of blood vessels within the body. However, this method has drawbacks insofar as a prior estimation of the rate of circulation in the vessels is necessary. In addition, since the phase is a quantity expressed to within $2\pi$, an ambiguity remains regarding the effective rate deduced from a magnetic resonance signal.

These first two methods are therefore based on characteristics associated with a displacement, in particular of blood in the body. They thus find an application in the angiography field. On the other hand, they do not make it possible to detect a particular static or virtually static element of the body. They cannot therefore be used as a basis for the formation of an image for a particular organ or for a particular cell type.

A third method has made a name for itself in the last few years in the angiography field. It comprises a step consisting in injecting a contrast product into a body. In general, the contrast product used is gadolinium attached to a chelating agent such as DOTA (or tetraazacyclododecane tetraacetate) or DTPA (or diethylenetriamine pentaacetate). The chelating agent is a molecular cage that surrounds the gadolinium and makes it possible to limit its toxicity with respect to the body into which it is injected. The effect of this product is to decrease the relaxation time of the protons that are in proximity. Specifically, the contrast product contains single unpaired electrons which have a paramagnetic effect that acts on the water protons.

This increase in proton relaxation makes it possible to limit the saturation in the zone where the injected product is located. The resulting magnetic resonance signal is therefore greatly increased. Conversely, the protons that are not in immediate proximity to the gadolinium keep an unchanged relaxation time and therefore generate a lower magnetic resonance signal.

Initially after injection, the contrast product moves in the blood vessels without being absorbed by the surrounding tissues. Detection of the magnetic resonance signals therefore makes it possible to distinguish between the blood vessels and the surrounding tissues and also to form an image revealing this distinction.

However, this technique also has drawbacks. In particular, paramagnetic gadolinium, in addition to its action on proton relaxation time, creates magnetic induction microgradients that result in local distortions of the magnetic induction to which the body is subjected. The frequencies of the waves transmitted are dispersed. This effect can result in the loss of certain signals. When the magnetic resonance signals are used to form an image of a zone of the body in question, said image will therefore be difficult to interpret. This results in the spatial resolution of the images obtained by this technique being limited: this method does not allow complete suppression of the signals derived from tissues lacking contrast product.

An object of the present invention is to provide a method for acquiring magnetic resonance signals that limits the problems encountered in the above techniques.

Another object of the invention is to enable acquisition of the signals from a selected observed zone, independent of its type. For example, the observed zone may contain substantially mobile or substantially immobile protons. It may be a blood vessel or a vascularized network, but also an organ, a group of cells, or the like.

SUMMARY OF THE INVENTION

The invention thus proposes a method for acquiring electromagnetic signals received from at least one part of a body placed in a system comprising means for generating a magnetic induction $B_0$, said magnetic induction comprising gradients in certain directions in space, means for transmitting radio frequency wave pulse sequences perpendicular to the magnetic induction $B_0$ in a range of adjustable frequencies, and means for detecting electromagnetic signals received from said body part. The method comprises the following steps:

a) injecting, into said body part, an amount of contrast product capable of being temporarily fixed in or of passing through an observed zone of said body part, said contrast product comprising at least one element capable of causing a chemical shift of a resonance frequency of water hydrogen protons;

b) exciting said body part by means of a radio frequency wave pulse sequence in a range of frequencies adjusted according to the magnetic induction $B_0$ and to the chemical shift for at least some of said radio frequency waves;

c) detecting, coherently with the excitation of step b), electromagnetic signals received from said body part, said signals corresponding substantially to magnetic resonance signals of the protons of the observed zone having undergone the chemical shift.

The chemical shift provided by the contrast product brings about a shift in the resonance frequency of the hydrogen protons contained in the water in proximity to the injected contrast product. This shift in frequency makes it possible to obtain a selective signal from the protons chemically shifted during a radio frequency-based solicitation taking into account this shift. Such selective signal can advantageously be used as a basis for forming an image.

The observed zone envisioned here may be of various types, for instance a blood vessel, a group of cells expressing a gene, a tumor zone, or the like.

The invention also proposes a contrast product intended to be injected into at least one part of a body for the purpose of acquiring electromagnetic signals from said body part. This product comprises at least one element capable of causing a chemical shift of a resonance frequency of water hydrogen protons.

The element included in the contrast product may advantageously be a lanthanide, for example dysprosium, praseodymium and/or europium, optionally attached to a chelating agent, or any other element capable of inducing a modification of the resonance frequency.

BRIEF DESCRIPTION OF THE DRAWING

The single FIGURE is a simplified representation of an observed zone to which the invention is applied.

According to the invention, an amount of contrast product is injected into a body 4, which may be, for example, a human or animal body, but which may also be an inert body. The injection is performed in such a way that the contrast product is fixed at least temporarily in or passes through an observed zone 1. In the case of a human body, for example, the contrast product may be injected intravenously. The observed zone may then comprise a blood vessel 2 through which the contrast product passes, and also the tissues 3 that surround this vessel.

DESCRIPTION OF PREFERRED EMBODIMENTS

The various steps of the method described below must take place rapidly after injection of the contrast product so that the latter remains essentially contained in the zone for which it is desired to recover a magnetic resonance signal, i.e., in the example illustrated in the FIGURE, the vessel 2, but not the tissues 3 that surround it.

The contrast product used according to the invention has the property of effecting a chemical shift on the hydrogen protons that are in proximity thereto. This is because such a product contains atoms whose electron cloud is capable of modifying the local magnetic induction experienced by the nucleus observed. The protons that are in proximity to the contrast product, for example the protons contained in the hydrogen of the water of the blood circulating in the vessel 2, are subjected to this magnetic induction.

If the protons in contact with the contrast product are subjected to a magnetic induction $B_0$, their resonance frequency is no longer the Larmor frequency $v_0$ proportional to the amplitude of $B_0$, but a frequency $v_1$ that is shifted with respect to $v_0$. By way of illustration, if the chemical shift created by the contact product is 3.5 parts per million (ppm), the following frequency relationship is obtained: $v_1-v_0=3.5\times 10^{-6}\times v_0$. For a magnetic induction $B_0=1.5$ T, the Larmor frequency $v_0=63$ MHz, and a frequency shift $v_1-v_0\approx 220$ Hz is therefore obtained between the protons that are in proximity to or not in proximity to the contrast product.

It should be noted that the chemical shift property is not inherent to all products. In particular, gadolinium, commonly used as a contrast agent for its properties of reducing the proton relaxation time as explained in the introduction, causes virtually no chemical shift. On the other hand, three other elements of the lanthanide family are notable for their chemical shift action. These are dysprosium (Dy), praseodymium (Pr) and europium (Eu).

For example, as regards dysprosium, the chemical shift created $\Delta$(in ppm) is proportional to the concentration of dysprosium (in millimoles per liter) with a proportionality coefficient of 0.185, i.e. $\Delta=0.185*[Dy]$.

Conventionally, cages are used to surround the lanthanides in order to limit their toxicity, as was the case for gadolinium.

These cages are typically chelating agents such as DOTA or DTPA. The contrast product used is therefore advantageously a lanthanide chelate capable of generating a chemical shift, such as Dy-DOTA, Dy-DTPA, Pr-DOTA or Pr-DTPA.

The body 4 is placed, immediately before or after injection of the contrast product, in a system that surrounds a part of the body and that is capable of generating a high-amplitude magnetic induction $B_0$. This induction comprises gradients in principle directions in space according to the type of information that it is desired to acquire. For example, if it is desired to obtain magnetic resonance signals for elementary volumes in three-dimensional space, it will be advisable to introduce coding gradients $G_x$, $G_y$ and $G_z$ for the magnetic induction $B_0$ in three main perpendicular directions (x, y, z) in space, in a manner known in itself. By means of this technique, magnetic induction values that are different between elementary volumes of the body 4 are ensured.

The system in which the body 4 is placed also has a transmitter of radio frequency wave pulse sequences in a range of adjustable frequencies that may be more or less selective, according to the duration of transmission of the corresponding waves. These RF waves are transmitted perpendicular to the direction of the magnetic induction $B_0$. When a wave is transmitted at a frequency corresponding to the proton resonance frequency, said protons are then taken out of their equilibrium position in a direction close to that of the induction $B_0$, and then they gradually return to this equilibrium position.

According to the invention, the protons in proximity to the injected contrast product have a resonance frequency that is shifted with respect to the usual Larmor frequency. Advantage is then taken of this particularity in order to recover electromagnetic signals only from these chemically shifted protons.

For this, at least two methods can be envisioned. According to a first embodiment, a radio frequency wave pulse sequence is transmitted with a frequency adjusted selectively to the value of the frequency shifted due to the chemical shift, i.e. $v_1$ according to the notation employed above.

At the end of each transmission of a radio frequency wave pulse sequence, a reception module detects and evaluates the transmitted magnetic resonance signal. According to the principle explained above, only the protons in the vessel 2 of the example illustrated in the FIGURE come into resonance and generate a magnetic resonance signal. The other protons that are not in proximity to the injected contrast product, i.e. typically the protons present in the tissues 3, generate virtually no signal.

Thus, if an image of the observed zone 1 is realized, for example in a spatial plane, by taking advantage of the magnetic induction gradients, and with each point of the image corresponding substantially to a detected signal value, as a function of its geographical position in the plane under consideration according to a conventional spatial coding, the zones where the contrast product has been fixed can be clearly distinguished. An image is thus obtained, where the vessel 2 will be visible, while the tissues 3 will be invisible.

This embodiment is therefore entirely advantageous. However, it has the drawback of requiring a sequence of radio frequency transmissions that are selective with respect to frequency, which means that a considerable transmission time is needed. When the observed zone is large, the signal acquisition time may prove to be disadvantageous.

A second advantageous embodiment makes it possible to limit the magnetic resonance signal acquisition time. It consists in using a radio frequency wave pulse transmission sequence comprising a first series of selective wave pulses adjusted to a frequency corresponding substantially to the Larmor frequency for the water protons not chemically shifted, i.e. the protons of the tissues 3 in the example illustrated. These waves are transmitted with a sufficient duration to saturate the protons concerned, to such an extent that these protons no longer transmit any significant magnetic resonance signal at the end of the first series of wave pulses.

The radio frequency wave transmission sequence also comprises a second series of wave pulses that are relatively nonselective in terms of frequency, each wave of the sequence being transmitted over a short period of time. The range of frequencies covered by these waves comprises the resonance frequency of the chemically shifted protons, i.e. of the protons of the vessel 2. Thus, only the latter protons will come into resonance upon transmission of the second series of waves, the protons of the tissues 3 being saturated. This makes it possible to rapidly receive the signals coming from only the protons of the vessel 2.

In this way, the signals transmitted by the chemically shifted protons are isolated with precision. Furthermore, the contrast products used with dysprosium, praseodymium or europium have only a limited action on the distortion of the magnetic induction in the observed zone, through the creation of magnetic induction microgradients, unlike gadolinium. The images obtained by applying this technique therefore potentially have a greater spatial resolution than the known techniques using gadolinium chelates.

As was described above, the chemical shift engendered by injection of the contrast product, for example dysprosium, as a function of the concentration of the latter, is known. This prior knowledge can make it possible to precisely select the frequency of the wave to be transmitted in the observed zone. However, in another advantageous embodiment, it is possible to determine the frequency resulting from the chemical shift without prior knowledge. For this, the observed zone 1 of the body 4 is subjected to successive waves in a broad spectrum of radiofrequencies and the magnetic resonance signals generated by the observed zone in reaction to each of these waves are detected. The main frequency that causes the protons of the observed zone having undergone the chemical shift to come into resonance is then deduced therefrom.

So far, the observed zone 1, illustrated in the FIGURE, has been taken to comprise a blood vessel 2 surrounded by tissues 3. This representation makes it possible to envision applications of the present invention in the angiography field.

However, the invention can also be applied to other types of observed zones. In particular, the observed zone may comprise a target, which may, for example, be a cell, a molecule, a protein, or a group of targets of the body under consideration, such as a group of cells expressing a gene.

In this situation, a known targeting molecule is advantageously attached to the contrast product injected into the body, such that the latter is temporarily fixed in the target. The steps described above can then be carried out so as to acquire magnetic resonance signals coming from the target only, with the exclusion of certain surrounding tissues in which the contrast product has not been fixed. This embodiment is particularly advantageous and finds applications in the field of cellular and molecular imaging, for example for studying gene expression in vivo, for localizing a particularly biological activity, or the like.

The observed zone may also be a zone of angiogenesis, for example a tumor zone. Such a zone generally comprises a vascularized network, the vascularization index of which gives an indication regarding the malignant or benign nature of the tumor.

In one embodiment, the invention makes it possible to determine such a vascularization index. To this effect, the lanthanide chelate used as contrast product is injected so as to be temporarily fixed in the tumor zone. As described above, it is possible to realize a spectrum in this observed zone, i.e. to transmit successive radio frequency waves within a broad spectrum of frequencies. The resonance frequency of the protons located in the vascularized network present in the tumor zone is deduced therefrom, this resonance frequency being substantially the frequency for which magnetic resonance signals were received (outside the conventional Larmor frequency of the water protons not having experienced a chemical shift). Advantageously, this operation can be carried out several times at successive moments so as to make it possible to monitor any change in the time of this resonance frequency.

As was indicated above, the chemical shift caused by the contrast product, for example based on dysprosium, is proportional to the concentration of dysprosium. Determination of the resonance frequency in the tumor zone, which is itself proportional to the chemical shift, then gives an indication of the concentration of contrast product fixed in the observed zone. It is therefore understood that this indication constitutes a vascularization index that can be taken into account in a subsequent analysis of the tumor.

As in the previous cases, the magnetic resonance signals coming from the tumor zone can be acquired so as to characterize in greater detail the vascularized network present in the tumor zone. An image of the zone can also be obtained from this acquisition.

The invention claimed is:

1. A method for acquiring electromagnetic signals received from at least one part of a body placed in a system comprising means for generating a magnetic induction $B_0$, said magnetic induction comprising gradients in certain directions in space, means for transmitting radio frequency wave pulse sequences perpendicular to the magnetic induction $B_0$ in a range of adjustable frequencies, and means for detecting electromagnetic signals received from said body part, the method comprising the following steps:
   a) injecting, into said body part, an amount of contrast product capable of being temporarily fixed in or of passing through an observed zone of said body part, said contrast product comprising at least one element capable of causing a chemical shift of a resonance frequency of water hydrogen protons of said body part;
   b) determining a new resonance frequency, shifted with respect to the Larmor frequency ($v_0$) for the water hydrogen protons of said body part nearby said contrast product;
   c) exciting said body part by means of a radio frequency wave pulse sequence in a range of frequencies adjusted according to the magnetic induction $B_0$ and to the new resonance frequency determined at step b) resulting from the chemical shift of the resonance frequency of water hydrogen protons for at least some of said radio frequency waves;
   d) detecting, coherently with the excitation of step c), electromagnetic signals received from said body part, said signals corresponding substantially to magnetic resonance signals of the water hydrogen protons of the observed zone of said body part having undergone the chemical shift of the resonance frequency.

2. The method as claimed in claim 1, in which the element capable of causing a chemical shift of a resonance frequency of water hydrogen protons and included in the contrast product comprises a lanthanide.

3. The method as claimed in claim 2, in which the lanthanide is chosen from at least one of dysprosium, praseodymium and europium.

4. The method as claimed in claim 1, in which the contrast product also comprises a cage that incorporates the element capable of causing a chemical shift of a resonance frequency of water hydrogen protons.

5. The method as claimed in claim 1, also comprising a step consisting in forming an image from the electromagnetic signals received from said body part that are detected, according to a spatial coding dependent on the gradients of said magnetic induction.

6. The method as claimed in claim 1, in which said observed zone comprises a group of blood vessels.

7. The method as claimed in any one of claims 1 to 5, in which the contrast product is injected with a targeting molecule capable of being fixed to at least one target that is part of the observed zone.

8. The method as claimed in claim 7, in which the target is a group of cells expressing a gene of said body part.

9. The method as claimed in claim 1, in which the observed zone comprises a tumor zone of said body part and in which an indication of the concentration of contrast product fixed in or passing through the tumor zone is deduced from the resonance frequency of the protons of the observed zone having undergone the chemical shift of a resonance frequency, this indication being a vascularization index for said tumor zone.

10. The method as claimed in claim 4, wherein the contrast product is tetraazacyclododecane tetraacetate or diethylenetriamine pentaacetate.

11. The method as claimed in claim 1, wherein the contrast product is tetraazacyclododecane tetraacetate or diethylenetriamine pentaacetate.

12. A method for acquiring electromagnetic signals received from at least one part of a body placed in a system comprising means for generating a magnetic induction $B_0$, said magnetic induction comprising gradients in certain directions in space, means for transmitting radio frequency wave pulse sequences perpendicular to the magnetic induction $B_0$ in a range of adjustable frequencies, and means for detecting electromagnetic signals received from said body part, the method comprising the following steps:
   a) injecting, into said body part, an amount of contrast product capable of being temporarily fixed in or of passing through an observed zone of said body part, said contrast product comprising at least one element capable of causing a chemical shift of a resonance frequency of water hydrogen protons of said body part;
   b) exciting said body part by means of a first radio frequency wave pulse sequence in a range of frequencies adjusted to a frequency corresponding substantially to the Larmor frequency for water hydrogen protons not chemically shifted with a duration long enough to saturate said protons, so that these protons no longer transmit any significant magnetic resonance signal at the end of the first radio frequency wave pulse sequence;
   c) exciting said body part by means of a second radio frequency wave pulse sequence that is relatively non-selective in terms of frequency;
   d) detecting, coherently with the excitation of step c), electromagnetic signals received from said body part, said signals corresponding substantially to magnetic resonance signals of the water hydrogen protons of the observed zone of said body part having undergone the chemical shift of the resonance frequency.

13. The method as claimed in claim 1, wherein the shift between the new resonance frequency and the Larmor frequency is proportional to the concentration of the contrast product.

14. The method as claimed in claim 13, wherein the shift between the new resonance frequency and the Larmor frequency is obtained by the following relationship:

$$v_1 - v_0 = C \times 10^6 \times v_0$$

wherein $v_1$ is the new resonance frequency, $v_0$ is the Larmor frequency, and C is the concentration in parts per million (ppm).

15. The method as claimed in claim 1, wherein the determining step comprises subjecting said body part to successive waves in a broad spectrum of radiofrequencies;

detecting the magnetic resonance signals generated by the body parts in reaction of each of these waves; and determining the main frequency that causes the protons of the observed zone having undergone the chemical shift to come into resonance.

* * * * *